United States Patent [19]

Grendol et al.

[11] 4,425,669
[45] Jan. 17, 1984

[54] SAFETY GOGGLE

[75] Inventors: Clark L. Grendol, Sturbridge, Mass.; Richard H. Seager, Mystic, Conn.

[73] Assignee: American Optical Corporation, Southbridge, Mass.

[21] Appl. No.: 346,450

[22] Filed: Feb. 8, 1982

[51] Int. Cl.³ .............................................. A61F 9/02
[52] U.S. Cl. .................................................... 2/436
[58] Field of Search ................ 2/436, 437, 439, 442, 2/443, 446, 447, 448, 449, 451

[56] References Cited

U.S. PATENT DOCUMENTS

| 202,130 | 8/1865 | Mitchell | D57/1 |
| 1,225,548 | 5/1917 | Willson et al. | 2/449 |
| 2,274,791 | 3/1942 | Huggins | 2/444 |
| 2,296,634 | 9/1942 | Fink | 2/12 |
| 2,342,766 | 2/1944 | Stiano | 2/437 |
| 2,382,962 | 8/1945 | Courtney | 2/448 X |
| 2,582,345 | 1/1952 | Moeller | 2/446 X |
| 2,654,090 | 10/1953 | Christensen et al. | 2/436 |
| 2,668,291 | 2/1954 | Schauweker | 2/14 |
| 4,250,577 | 2/1981 | Smith | 2/9 X |
| 4,271,538 | 6/1981 | Montesi et al. | 2/439 |

FOREIGN PATENT DOCUMENTS 150848  9/1981  German Democratic Rep. .... 2/436

Primary Examiner—Peter P. Nerbun
Attorney, Agent, or Firm—Kenway & Jenney

[57] ABSTRACT

A safety goggle including a one-piece wrap-around front with hinged temples continuing rearwardly therefrom. The goggle features improved anti-fogging ventilation and universal nasal area face fitting.

5 Claims, 7 Drawing Figures

SAFETY GOGGLE

BACKGROUND OF THE INVENTION

1. Field of the Invention

The present invention relates to safety goggles more particularly of the lightweight, wrap-around type designed for protection against flying objects or particles.

2. Discussion of the Prior Art

Safety goggles of varying types of which U.S. Pat. Nos. 1,225,548; 2,274,791 and 2,668,291 are exemplary interfere with peripheral vision when worn and suffer the drawbacks of internal fogging particularly the structures of U.S. Pat. Nos. 2,274,791 and 2,668,291. These latter structures offer minimal, if any, ventilation, i.e. they lack provision for adequate circulation of air through the space between a wearer's face and the goggle front.

Improvement of peripheral vision in safety goggles can and has been accomplished to varying degrees with wrap-around goggle designs, e.g. as in U.S. Pat. Nos. 2,296,634 and Des. 202,130. These structures, however, fail to provide the usually desired and often required protection against injury from upwardly or downwardly flying objects, particles and/or dusts. This protection and improved peripheral vision have, nevertheless, been at least partially accomplished with the design of safety spectacles disclosed in U.S. Pat. No. 4,271,538. Lacking there, however, is provision for avoidance of lens fogging under most conditions of use and in particular the avoidance of fogging adjacent the brow and nasal portion of the goggle front.

In addition to the failure of prior art devices to overcome the above drawbacks is the further shortcoming of heretofore nosepiece design which prevents universal application to the various encountered nose sizes and shapes, i.e. at least to the extent of not accomplishing optimum comfort and closeness of fit in all cases.

In view of the above, a principal object of this invention is to accomplish improved wearing comfort in safety goggles.

More specifically, the present invention aims to accomplish improved goggle ventilation during wearing with optimum comfort of facial fit, the latter being especially related to improvement in goggle nosepiece design and the former to improvement in goggle brow and temple portion design.

Another object is to provide for simple and economical goggle nosepiece replacement.

Other objects and advantages of the invention will become apparent from the following description.

SUMMARY OF THE INVENTION

Objects and advantages of the invention are accomplished with the provision of a one-piece wraparound goggle front, endpieces of which are designed to extend beyond the positions of extreme peripheral vision of a wearer's eyes and to which rearwardly extending temples are attached. The temples and brow portions of the goggle front are designed to provide a close fit with corresponding portions of the wearer's head for protection against flying particles. At the same time, provision is made adjacent the adjoinment of temples and front for entrance of air into the space between the face and goggle front without admission of particles of harmful size. This ventilation of the goggle is accomplished in air scoop fashion and is rendered effective in its intended purpose by venting space provided in the goggle brow portion, i.e. above the wearer's nose so that air entering a temple air scoop crosses the corresponding half of the goggle front exiting through the brow venting space. By such means, the usual nasal area fogging is avoided.

Further featured in the present construction is a readily replaceable soft nosepiece which is universally conformable to comfortable fitting against the various nose shapes and sizes encountered in the field.

Details of the invention will become more readily apparent from the following description when taken in conjunction with the accompanying drawings in which.

DESCRIPTION OF THE PREFERRED EMBODIMENTS

Figure 1:
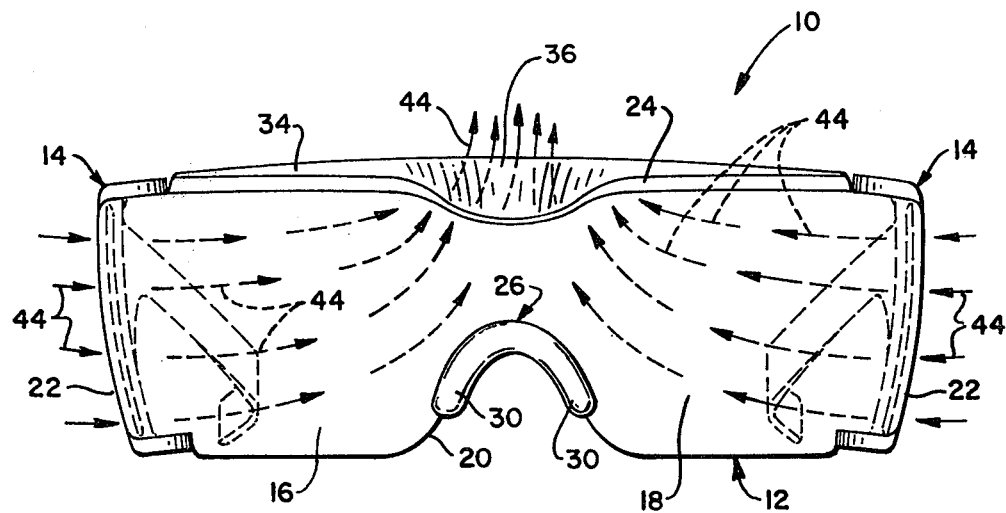
FIG. 1 is a front elevational view of a preferred embodiment of the invention.

Referring to the drawings, goggle 10 comprises front 12 molded or otherwise formed of a polycarbonate or similarly suitable material and temples 14 molded or otherwise formed of nylon, i.e. the somewhat different materials avoid squeeking noises during pivoting of the temples. Otherwise, the front 10 and temples can be formed of like materials.

Figure 6:
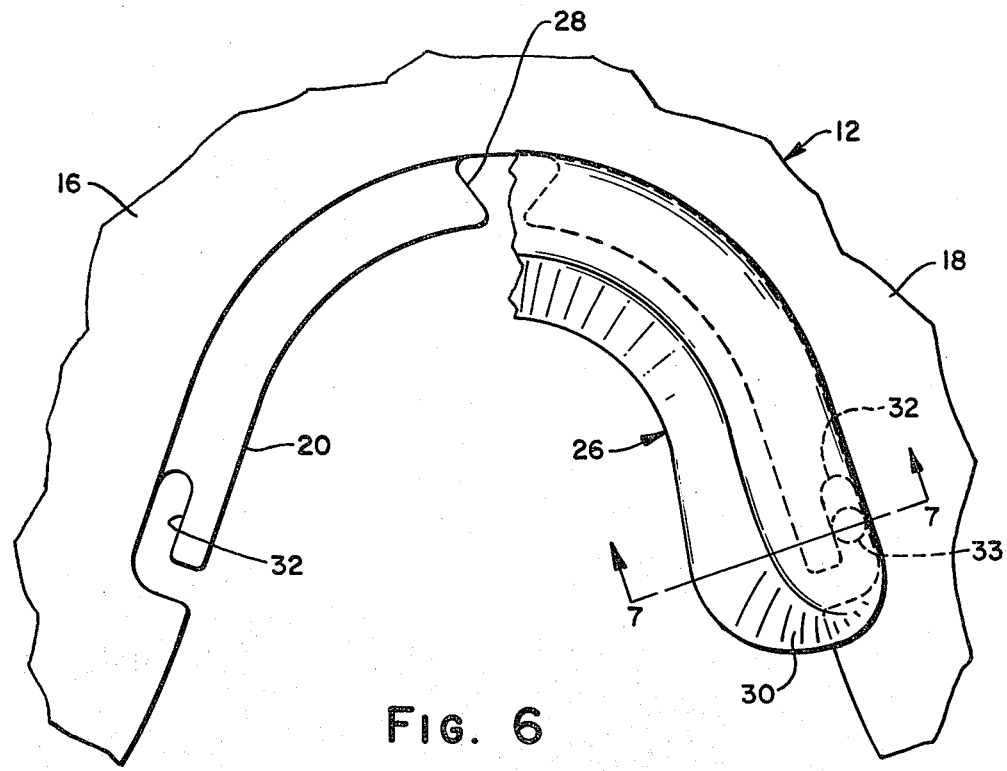
FIG. 6 is an enlarged front elevational view of the nasal area of the present goggle with a portion thereof broken away for clarity of illustration of details.
Figure 7:
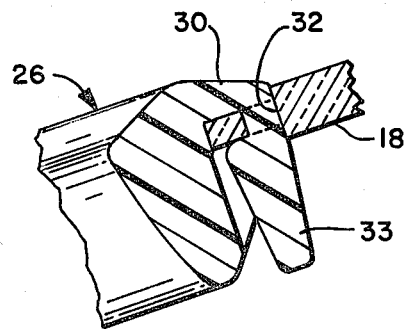
FIG. 7 is a cross-section taken along lines 7—7 of FIG. 6 looking in the direction of the arrows.

Front 12, of one piece construction, includes right and left forward viewing lens areas 16, 18 with a nasal recess 20 therebetween, wrap-around endpieces 22 and a rearwardly directed brow portion 24. Nasal recess 20 supports nosepiece 26 formed of a molded soft material such as silicon rubber or an equivalent. Nosepiece 26 is dovetailed into recess 28 of front 12 (FIG. 6) with depending ends 30 attached in bayonet slots 32. Circular openings may be substituted for slots 32. A tab 33 extending rearwardly from nosepiece 26 adjacent each of its ends 30 (FIG. 7) is hooked into a respective slot 32 or pulled through a correspondingly positioned circular opening if circular openings are used. Material of front 12 extending about the portion of nasal recess 20 which receives nosepiece 26 is thinned as shown in FIGS. 6 and 7 for intimate nosepiece fitting and improved goggle aesthetics. This thinning of the goggle front may, however, be dispensed with and a nosepiece molded thereinplace as an integral part of front 12 as a substitute for nosepiece 26, if desired.

Brow portion 24 of front 12 extends rearwardly of lens areas 16, 18 to upturned lip 34 which is intended for engagement with a wearer's forehead. Centrally of lip 34 is a forwardly directed relief 36 which provides a ventilation opening between the head and front 12, i.e. the space between broken line 38 and relief 36 permits ventilation of the spaces between lens areas 16, 18 and a wearer's face for avoidance of goggle front fogging as will become more readily apparent from the following.

Figure 2:
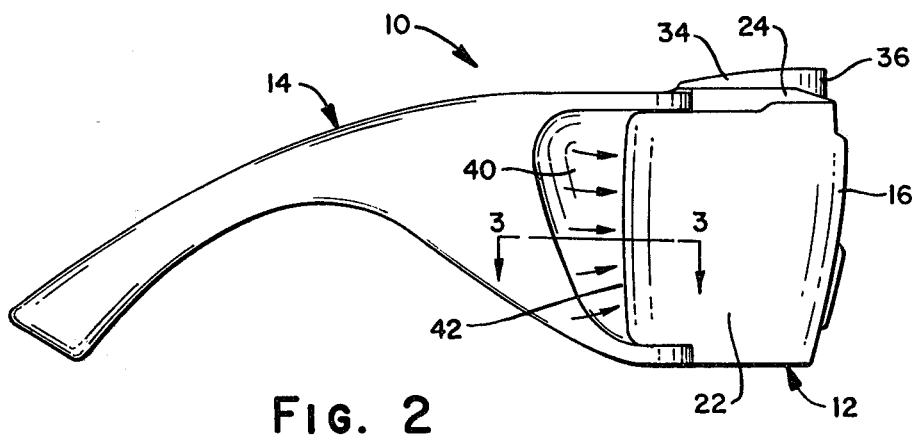
FIG. 2 is a side view of the goggle of FIG. 1.
Figure 3:
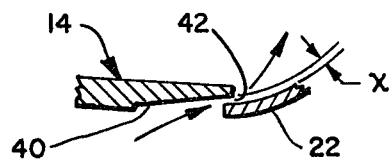
FIG. 3 is a fragmentary cross-sectional view taken approximately along line 3—3 of FIG. 2.
Figure 4:
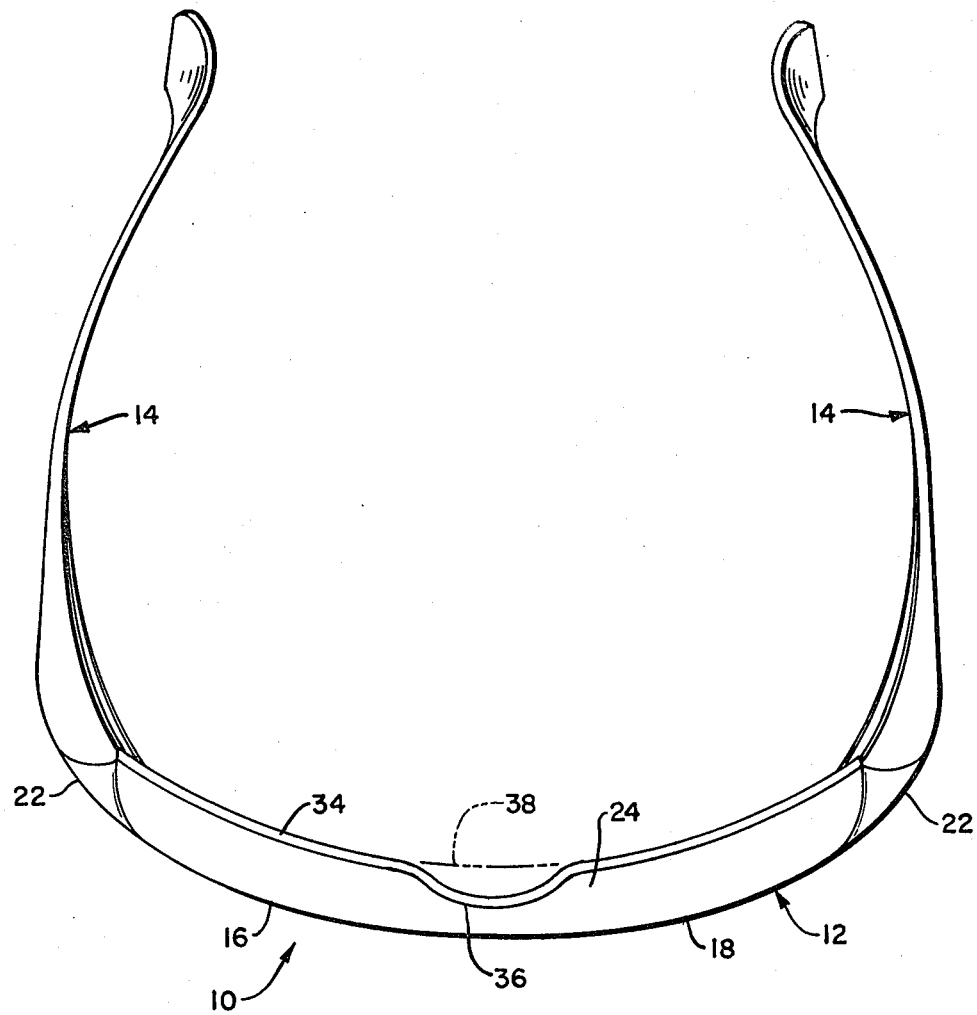
FIG. 4 is a top plan view of the goggle.
Figure 5:
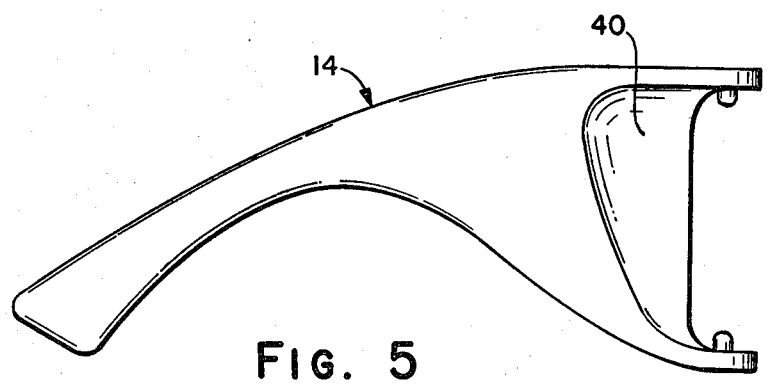
FIG. 5 is a side view of a temple shown detached from the goggle front for clarity of illustration of its construction.

Functioning with relief 36 of brow portion 24 are air scoops 40 (FIGS. 2, 3 and 5) in temples 14 which afford vertically elongated air entrance openings 42, one of which is shown in FIGS. 2 and 3. With each opening 42 extending approximately from top to bottom of scoop 40, e.g. over a length of approximately 1¾ inches in each case, optimum goggle front ventilation is accomplished without sacrifice of flying particle protection. In this connection, the width of opening 42 is preferably held to a dimension X (FIG. 3) of approximately 0.040 inch.

With goggle 10 applied to the face, air between the face and lens areas of front 12, warmed by the wearer, rises outwardly through the opening provided by relief 36 allowing cooler outside air to enter through scoops 40 and travel across lens areas 16, 18 as indicated by arrows 44 (FIG. 1). This prevents lens fogging particularly in the heretofore troublesome nasal areas.

In addition to air scoops 40, temples 14 feature upper and lower turned-in edges 46, 48 which provide for close fitting against the head and protection against entrance of external foreign matter into temporal regions of the goggle. Additionally, and in a unique and simple fashion, pivot pins integral with the temple construction in each case are adapted to snap-fit into corresponding openings in the endpieces 22 of front 12 for hinging the temples thereto. It should be understood, however, that other forms of temple hinging may be used if desired.

The foregoing is believed to illustrate the improvements in facial fitting and general aesthetics afforded by the present goggle 10 and more particularly its highly significant anti-fogging design features. It should be understood, however, that various modifications and adaptations of the precise form of the invention described above may be made to suit particular requirements and it is intended that all modifications which incorporate the novel concept disclosed are to be construed as coming within the scope of the following claims or range of equivalency to which they are entitled.

We claim:

1. A safety goggle comprising the combination of a one-piece wrap-around front having endpieces extending beyond portions of extreme peripheral vision of a wearer of the goggle, a rearwardly extending temple pivotally attached to each of said endpieces and each temple having an outer air scoop adjacent its connection to a respective endpiece, said air scoop providing an elongated generally vertically oriented air inlet for ventilating the space between a goggle wearer's face and said goggle front, said inlet being a passage oriented towards said space between the goggle wearer's face and said goggle front, and said front including a rearwardly directed brow portion with nasal area relief affording air exiting space for effecting said goggle front ventilation.

2. A safety goggle according to claim 1 wherein said goggle front further includes a nasal recess and nosepiece fixed thereto, said nosepiece being of soft, shape-conformable material providing universal fitting of said goggle to various sizes and shapes of noses.

3. A safety goggle according to claim 2 wherein said nosepiece is readily removeable for replacement purposes.

4. A safety goggle according to claim 1 wherein said air inlets afforded by said temple air scoops extend along rearward terminii of said endpieces of said goggle front, said endpieces partially overlapping said air scoops when said goggle temples are in a position of use.

5. A safety goggle according to claim 4 wherein the openings of said air inlets are approximately 0.040 inch in width for prevention of flying object entrance.

* * * * *